United States Patent
Kerr (12) 
(10) Patent No.: US 10,441,251 B2
(45) Date of Patent: Oct. 15, 2019

(54) DRAINAGE SYSTEM FOR WOUNDS

(71) Applicant: Marshall Kerr, Carlsbad, CA (US)

(72) Inventor: Marshall Kerr, Carlsbad, CA (US)

(73) Assignee: PFM Medical, Inc., Carlsbad, CA (US)

(*) Notice: Subject to any disclaimer, the term of this patent is extended or adjusted under 35 U.S.C. 154(b) by 1006 days.

(21) Appl. No.: 14/191,320

(22) Filed: Feb. 26, 2014

(65) Prior Publication Data

US 2014/0243707 A1     Aug. 28, 2014

Related U.S. Application Data

(60) Provisional application No. 61/769,482, filed on Feb. 26, 2013.

(51) Int. Cl.
*A61M 1/00* (2006.01)
*A61B 10/00* (2006.01)

(52) U.S. Cl.
CPC ........... *A61B 10/00* (2013.01); *A61M 1/0003* (2013.01); *A61M 1/0007* (2014.02); *A61M 1/0015* (2014.02); *A61M 1/0023* (2013.01); *A61M 1/0031* (2013.01); *A61M 1/0086* (2014.02); *A61M 1/0027* (2014.02); *A61M 1/0088* (2013.01); *A61M 2205/584* (2013.01)

(58) Field of Classification Search
CPC ... A61B 10/00; A61M 1/0007; A61M 1/0015; A61M 1/0086; A61M 1/0003; A61M 1/0023; A61M 1/0031; A61M 1/0027; A61M 1/0088; A61M 2205/584
USPC ........................................................ 604/316
See application file for complete search history.

(56) References Cited

U.S. PATENT DOCUMENTS

| | | | | |
|---|---|---|---|---|
| 4,323,067 A | * | 4/1982 | Adams | A61M 1/06 604/346 |
| 4,925,447 A | * | 5/1990 | Rosenblatt | A61M 1/0011 604/133 |
| 5,073,172 A | * | 12/1991 | Fell | A61M 1/0003 604/119 |
| 5,238,217 A | * | 8/1993 | Fell | A61M 1/0031 137/907 |
| 6,261,276 B1 | * | 7/2001 | Reitsma | A61M 1/0023 604/319 |
| 7,153,294 B1 | * | 12/2006 | Farrow | A61M 1/0001 604/317 |
| 2007/0027433 A1 | * | 2/2007 | Garcia | A61M 1/0003 604/319 |
| 2009/0281509 A1 | * | 11/2009 | Gellis | A61M 1/0011 604/316 |
| 2012/0046624 A1 | * | 2/2012 | Locke | A61M 1/0001 604/319 |

FOREIGN PATENT DOCUMENTS

EP     0186783 A1 *  7/1986  ......... A61M 1/0023

* cited by examiner

*Primary Examiner* — Andrew J Mensh
(74) *Attorney, Agent, or Firm* — Donn K. Harms (57) ABSTRACT

A fluid drainage system is provided which is configured to engage with a drainage tube engaged with a drainage site with a patient. The container has an internal cavity with negative pressure to impart suction to the drainage tube and can be engaged to the drainage tube without loss of negative pressure during the process. Secondary containers may be engaged to restore negative pressure to the first container and remove fluid therefrom. Walls of the first container may be shaped to resist deflection due to high internal negative pressure.

6 Claims, 4 Drawing Sheets

DRAINAGE SYSTEM FOR WOUNDS

This application claims priority to U.S. Provisional Application No. 61/769,482 filed on Feb. 26, 2013 and is incorporated herein in its entirety by this reference.

BACKGROUND OF THE INVENTION

Field of the Invention

The present invention relates generally to wound drainage systems for human and animal patients. More particularly, it relates to a system having one or a plurality of engageable vacuum bottles having means for sealed communication of the vacuum or negative pressure in the internal cavity of the bottle container, with the fluid to be drained from a patient and with a secondary bottle providing an auxiliary communication of negative pressure.

Background of the Invention

During surgery and during recovery following such surgery, and in some cases as a treatment without surgery, it frequently becomes a requirement to evacuate fluid and other liquid such as wound secretions from the body of a patient. Such removal can be from an internal organ, a surgical site or position or from the site of a wound or other body site wherein fluid as been caused to collect.

In years past, vacuum pumps and other negative pressure generation devices have been employed. However, in the event of mechanical failure of the pump, or an electrical power failure causing cessation of pumping, such is not a preferred mode of treatment. Further, in line with modern efforts to control infection and remove potentially infectious materials from proximity to the patient and from the area of the hospital or medical facility, the use of containers having an interior cavity under negative pressure which will communicate suction when placed in communication with the body of a patient, and can then be disposed and removed with contents, has gotten more popular. Such containers, having an internal cavity with pre-positioned negative pressure therein, communicate a suction when engaged with one end of the tubing such as a catheter or other tubing. The suction communicating through the axial conduit of the tubing to a distal end, will evacuate fluids when they are positioned proximate to the distal end of the flexible tube such as positioned in the body of the patient, and into the container.

Such containers are conventionally sized from about 600 ml to 1000 ml and unlike mechanical vacuum systems which use pumps, these vacuum containers are provided with negative pressure formed within the internal cavity. Such containers when evacuated of air pressure thus provide a portable suction device which is easily replaced once the negative pressure reservoir is gone. They are also easily disposed to remove infected fluids from the treatment facility, and when filled wholly or partially, they may also be sent to labs for review of the fluids collected for the provision of medical reporting.

Current suction container devices employed in many hospitals are formed as a glass bottle with glass sidewalls which define an internal cavity which has been evacuated of atmosphere to form negative air pressure or a vacuum therein. The glass bottles have an opening which is capped, or otherwise sealed with a covering, to maintain the negative pressure within the cavity. Activation to communicate the suction from the container to the tubing employed for drainage involves piercing the cap or cover with a sharp needle or a provided piercing instrument.

While glass walled containers are excellent in maintaining their shape under high vacuum, they suffer from a number of problems when employed in the medical field. First, glass containers inherently are brittle on an impact and thus they break easily if dropped or struck by a glancing blow. Such a potential for breaking can be a severe problem for the medical facility should the bottle be broken or cracked by an impact and the liquid and/or other patient body secretions from the interior cavity are communicated to the facility floor or onto a bed.

Additionally, sampling the contents of a glass bottle is not easily accomplished. This is because glass walled containers conventionally only have one aperture to provide access to the interior cavity and that access is in a sealed communication with a tube or catheter.

Consequently, if a laboratory analysis of the interior cavity fluid contents is desired rather than accessing the interior cavity through an auxiliary aperture or conduit, the entire glass bottle must be sent to the laboratory where a technician can open it and sample the contents. In light of the potential for breaking during transport noted above, the need to take the entire bottle to a lab, and risk spreading infection if the bottle is dropped or struck during transport, is undesirable. Further, should a break occur, lab analysis of the patient secretions is further delayed while a new glass bottle is set up, pierced, engaged with a tube and sufficient secretions extracted.

An additional problem is from the need to use a sharp instrument to pierce the seal or cover of the single aperture of the glass bottle and quickly seal it to prevent total evacuation. Such is first a hazard to the user who must pierce the bottle, and later to the lab personnel who must remove the piercing component to sample fluid contents.

The sharp piercing instrument can easily cut or otherwise hurt medical personnel unfamiliar with using such. Additionally, if the cover of such a glass bottle is pierced, without first engaging a sealed tube to the piercing instrument, the vacuum in the bottle cavity can easily vent and the entire bottle rendered unusable by the entry of the exterior atmosphere immediately into the interior container.

Still further, glass containers have sidewalls which are not easily bored or drilled to allow the engagement of connectors to the bottle. This lack of additional openings to the bottle interior limits the ability of medical processionals and other users, to simply drain the contents of the interior cavity to a secondary container while concurrently reforming the vacuum in the bottle collecting fluids from a patient.

Still further, it can be hard to discern in conventional containers if they still have sufficient vacuum onboard to continue the suction-aided draining of a patient. This can occur when such bottles are on the floor next to the bed, which renders them hard to see from the doorway of the room, or in an overhead view, to determine their state.

As a result, there is a continuing unmet need for a wound and bodily fluid drainage system which overcomes the shortcomings of glass and other conventional drainage vacuum bottle systems. Such a system should allow for a vacuum container with at least one and preferably a plurality of easy opening and closure components for medical professionals to employ, for sealed access of the vacuum to an engaged tube or conduit. A plurality of closures is preferred to allow for sealing of the vacuum from the tube leading to the patient, and a sealing of the tube from the patient, in its communication to the access to the vacuum of the container.

Further, such an improved fluid draining system should provide easy but resealable access to the interior contents for taking lab samples, without the need to carry or move the container, to alleviate the dangerous practice of carrying a fluid-filled glass bottle through a medical facility. Still further, such an improved system should provide containers or bottles formed of lightweight polymeric or other plastic material with walls which are reinforced with ribs and/or of a thickness sufficient to maintain the structural integrity of the interior cavity, to maintain a vacuum of 600 to 700 hg/mm to eliminate the need for using current heavy glass containers.

Additionally, such a wound and fluid drainage system should be provided in a system of engageable components to give users options on draining the collection container connected to a patient. Employing such a system, users should be able to resupply a vacuum or negative atmosphere to a patient engaged collection container, without the need to disconnect such a patient-engaged container from the tube engaged with a patient. Finally, in addition to preferably multiple closures for the axial cavity of the tube communicating with the vacuum, an access to the interior cavity of the bottle should be provided for sampling or removing collected fluids without disconnecting the container from the patient or disengaging any hoses or sealed connectors.

Finally, such a plastic or polymeric suction container system, should provide an easily discerned status when viewed from above, as to whether the vacuum within is exhausted or not.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device and vacuum drainage system herein described and disclosed cures the shortcomings of the prior art through the provision of a system of engageable reservoir bottles and conduit or tubing interconnections, which employ lightweight reservoir bottles formed of polymeric materials which are lightweight. The bottles have wall surfaces defining an interior cavity which are structured to maintain structural integrity and resist a high vacuum within an interior cavity without deformation of the walls of the container. Multiple inlets and outlets may be provided to allow for fluid sampling, for drainage, or for communication of a new vacuum source to evacuate the collection bottle to allow continued use without disconnecting the patient.

The container herein, employable for collection of fluid from the patient, is provided with a plurality of closure components which allow the user to seal the tube from one or both of the patient end of the tube and the engagement of the tube with the interior cavity of the container. Two such closures are especially preferred in that they help to prevent accidental leakage of the vacuum during set up, or should a tube be removed. Additionally, an anti-backflow valve may also be provided to prevent fluid flow from draining from the proximal end of the tube engaged with the patient, unless that tube is in sealed communication with a vacuum sufficient to overcome the seal provided by the backflow valve.

A Y-connector is preferably positioned at the engagement of the tube communicating with the patient, and a flexible connector engaged with the inlet of the container. The Y-connector allows for communication of the vacuum to pull fluid from the patient through one conduit and provides a first access for fluid sampling via a needle-less valve adapted for a sealed engagement with a screw on or snap on needle-less syringe. This screw on syringe engagement allows for drawing a sample of the fluid communicated from the patient, without disengaging the container, or the need to carry it to the lab. An additional needle-pierceable self sealing access membrane may be provided alone or in combination with the first access. Such is located in a lower end of the bottle to allow sampling of fluid in the bottom of the interior cavity.

The system herein provides lightweight containers or bottles formed of lightweight polymeric or plastic material for easy carrying, shipment, and storage. The walls of the container are formed in a curve or may have additional arches formed into the curved walls to provide walls with sufficient structural integrity and rigidity to withstand the a vacuum of 600 to 900 hg/mm within the interior, and thus to eliminate the need for using current heavy glass containers.

Further, the system herein provides a kit of engageable components, which provide users the option to either replace the patient-engaged container when full, or, employ a second container having an equal or slightly higher vacuum therein and sealed tubes and attachments, which allow for the draining of fluid and reinstatement of the vacuum in the patient engaged container, without the need to disconnect the patient-engaged container from the tube engaged with a patient. One or a plurality of anti-backflow or reversionary valves may also be operatively positioned in the tubing or engaged connectors to prevent accidental spillage of significant amounts of fluid from tubes and allow flow therethrough only when a sufficient vacuum is present to draw fluid therethrough.

Further, a gauge is provided which is positioned in a top wall of the container which may have two modes of signaling the user that the vacuum within the container is exhausted. The gauge has an accordion style collapsing wall which collapses the elongation of the gauge when the container is at full vacuum. When the vacuum decreases, the walls unfold and elongate and can be colorized to show a signal when such occurs to allow the user viewing the bottle from a distance, to ascertain it needs changing or a vacuum recharge.

It is briefly noted that upon a reading this disclosure, those skilled in the art will recognize various means for carrying out these intended features of the disclosed fluid collection invention. As such it is to be understood that other methods, applications and systems employing multiple vacuum containers and tubing and connectors adapted to the task of interfacing the containers with each other may be configured to carry out these features and are therefor considered to be within the scope and intent of the present invention, and are anticipated.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present vacuum drainage system and disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The objects, features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive, examples of embodiments and/or features of the vacuum drainage system and components. It is intended that the embodiments and figures disclosed herein are to be considered illustrative rather than in any fashion limiting. In the drawings.

Other aspects of the present vacuum system for wound and fluid drainage invention shall be more readily understood when considered in conjunction with the accompanying drawings, and the following detailed description, neither of which should be considered limiting. It should be noted that components shown in the various figures could be employed with any mode of the device shown in other figures.

DETAILED DESCRIPTION OF THE PREFERRED EMBODIMENTS OF THE INVENTION

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Figures 1, 1A:
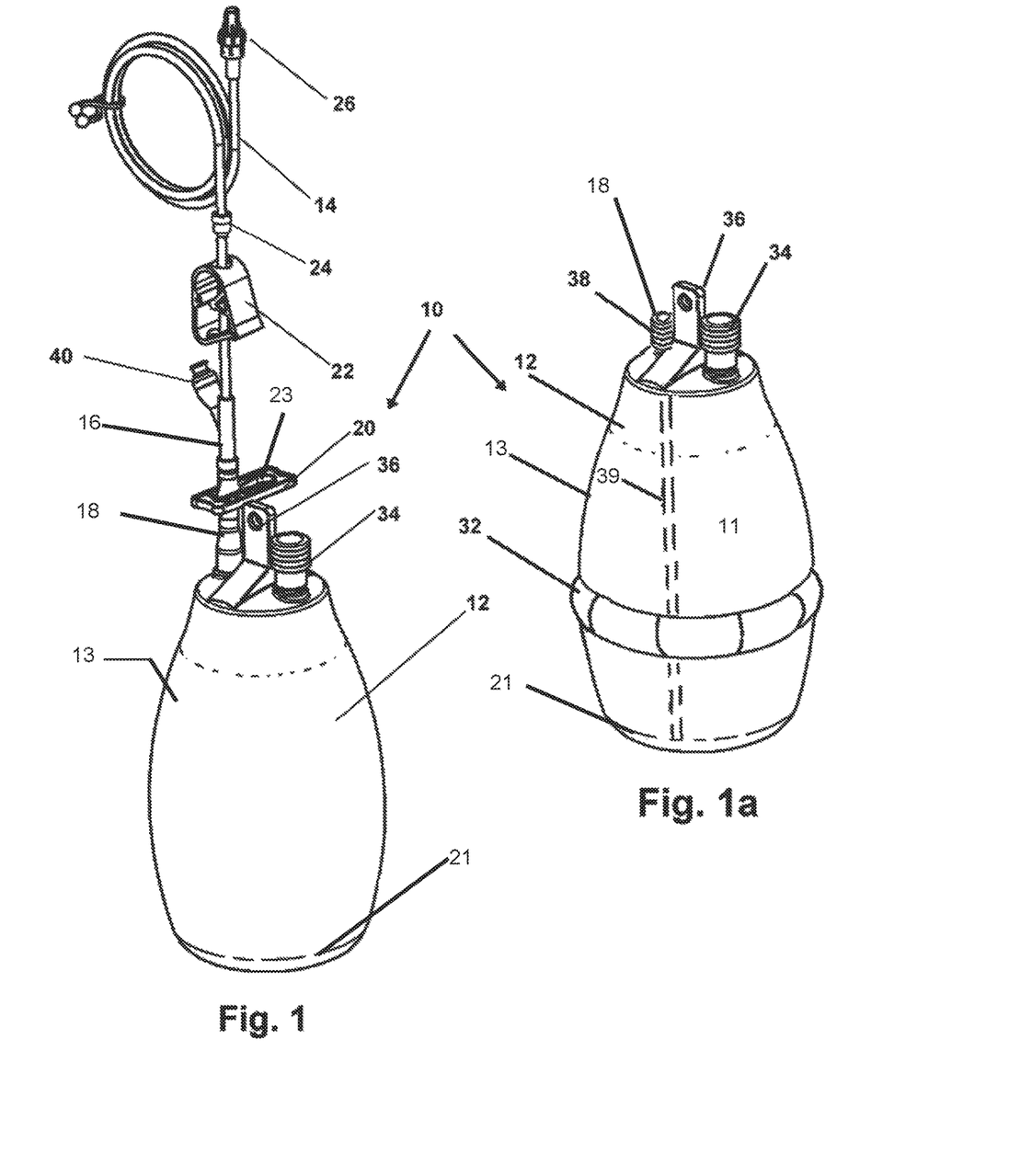
FIG. 1 depicts the patent-engageable vacuum drainage container and the tube providing the drainage conduit from the patient to the interior of the walled container in an as-used positioning with a lower end positionable on a support surface.
FIG. 1a shows another mode of the collection device where the container has a curved sidewall to resist bending under high vacuum and at least one annular or arched portion of the sidewall to add additional strength to resist inward deflection under high vacuum. Also shown are the accordion style vacuum gauge and an optional screw on connector providing communication to the interior cavity through an elongated conduit extending to position proximate the bottom surface of the container.

Now referring to drawings in FIGS. 1-6, wherein similar components are identified by like reference numerals, there is seen in FIG. 1, the device 10 which provides a vacuum drainage container 12 configured for an engagement with a the tube 14 or catheter at a first end in a sealed engagement. So engaged the container 12 provides for communication with the vacuum in the interior cavity of the container 12 and at a second or distal end to provide suction to the drainage conduit from the patient.

A Y-connector 16 bifurcates the tube 14 which is in sealed communication with the inlet 18 connector to the container 12 and which is formed of a compressible flexible tubular material defining an interior conduit which may be sealed by translation of clip 20 to place the narrower end of a slot 21 in a position to compress the soft wall of the inlet 18 to close an internal conduit and thereby seal the access to the interior of the container 12. The closure is especially helpful to maintain the vacuum during set up, and prevent accidental venting by unfamiliar users. However, the inlet 18 connector may also be formed with a biased seal which employs a spring or other bias, sufficient to resist the pull of the negative internal pressure of the container 12, until a mating connection to the inlet 18 connector is engaged which will bias the seal open, to communicate the negative pressure into the axial conduit of the connected 14. However the device may be made less expensively using the translating clip 21 to maintain a seal during engagement to a patient.

A second or compression clip 22 is also preferably provided to allow the user to deflect the sidewall of the tube 14 and seal the interior conduit, at the patient side end of the tube 14, and to also provide a secondary seal to prevent the vacuum in the container 12 from dissipating unintentionally.

Optionally provided is a backflow prevention valve 24 to seal communication through the axial conduit of the tubing 14 from any fluid flow when the tube 14 is disconnected from the container 12. When the vacuum from negative pressure relative to the atmosphere surrounding the exterior of the container 12, is communicated to the valve 24, it opens to allow fluid flow through the axial conduit of the tube 12 to the container 12. A connector 26 engaged with the axial passage of the tube 14 at the distal end of the tube 14 provides stiff connector for a removable engagement to a wound drainage component, such as a needle or inlet component placed in the proper position in the body of the patient for the intended fluid drainage.

The preferably curved sidewall 13 which arches from the bottom portion toward the top portion of the container 12 is especially important to allow the lightweight plastic or polymeric material forming the container 12 to resist inward deflection under a high vacuum. In all modes an interior surface of the sidewall 13 and the top and bottom portions, defines the volume of the interior cavity 11 as in FIG. 1a. Also in FIG. 1a another mode of the device 10 where the container 12 has the arched or curved sidewall substantially transparent sidewall 13 to resist bending under high vacuum as in all modes of the device, however also included is at least one annular outward or inward arched portion 32, formed into a central area of the sidewall 13 between the top or upper area of the container 12 and the opposite or bottom end of the container 12, to provide additional strength to the container to prevent the sidewall 13 on any side, from deflecting inward under high vacuum within the interior cavity 11, which of course would reduce the volume thereof as well as might damage the sidewall 13 from such a deflection.

Figure 6:
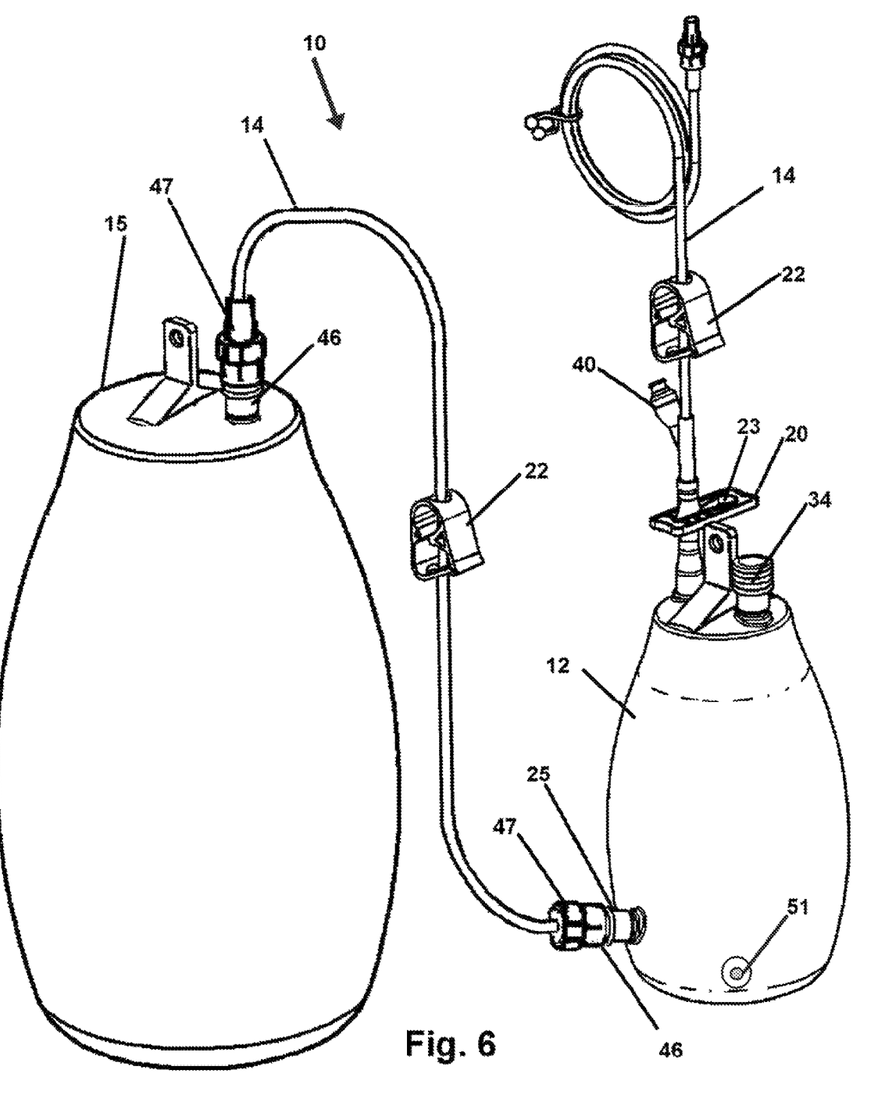
FIG. 6 shows another mode of the system herein wherein a first container is configured for patient engagement and a second container having a vacuum of sufficient strength to evacuate air and/or fluid from the first container, as well as reinstate the 600 to 900 hg/mm vacuum in the first container. Also shown is a small needle-pierceable component which self seals when pierced for fluid sampling.

Also shown are vacuum gauge 34, a hanger 36, and an optional screw-on or twist lock leur engagement or other sealable connector 38 providing a communication with the interior cavity of the container 12 for fluid sampling and/or removal and vacuum reinstatement by a secondary container (FIG. 6). As depicted in the figures, the container 12 has an as-used positioning with the end of the container with the hanger 36 and/or connector 26, to allow fluid drained from a patient to enter the interior cavity 11 though a top end which is higher in elevation than the opposite bottom 21 end, as shown.

Optionally, an interior tube 39 may extend from a sealed engagement at a first or top end, with the connector 38 to a distal end proximal to what is shown as the bottom 21 of the container 12 when it is engaged with a patient in an as-used position supported on the hanger 36 or sitting on a support surface under the bottom 21. With the interior tube 39, the container 12 allows for a sealed engagement of a syringe type device with the engageable component 40 of FIG. 1, and a drawing of fluid from the bottom 21 of the container 12 into the connected syringe which may be preferable to a sample of the fluid communicating from the tubing 14 which may be blocked off by the clip 22 during a bottom sampling. Additionally, in the mode of FIG. 6, the secondary bottle may be engaged to draw both fluid and atmosphere from the bottom 21 end, through the connector 38 and allow the container 12 to be replenished for operative use, without the need to remove it from engagement with a patient.

Figure 2:
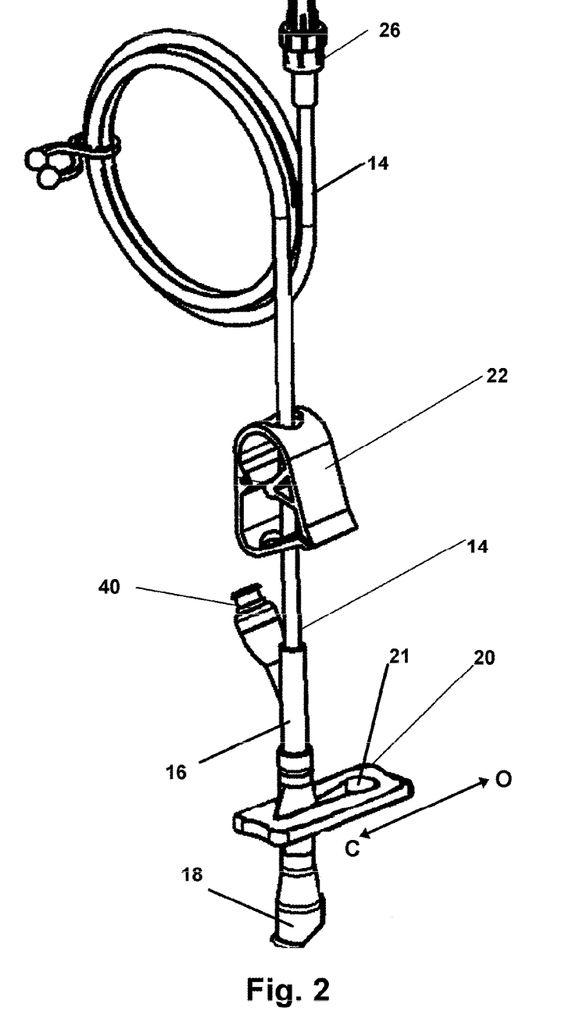
FIG. 2 depicts the tubing for engagement between the container and the patient having the Y-fitting providing a bifurcation of the internal conduit communicating in sealed engagement with the interior of the container.

FIG. 2 depicts an enlarged view of the tubing 14 for engagement between the container 12 and the patient and the Y-fitting 16 providing a bifurcation of the connection to the interior of the container 12. The syringe or tube connector component 40 allows for the sealed engagement of a needleless syringe to sample collected fluid as noted above, or a secondary tube 14 connected to a secondary container 14 such as in FIG. 6, instead of a lower connection, for evacuation of collected fluids from the container 14 and replenishment of the vacuum.

Figure 3:
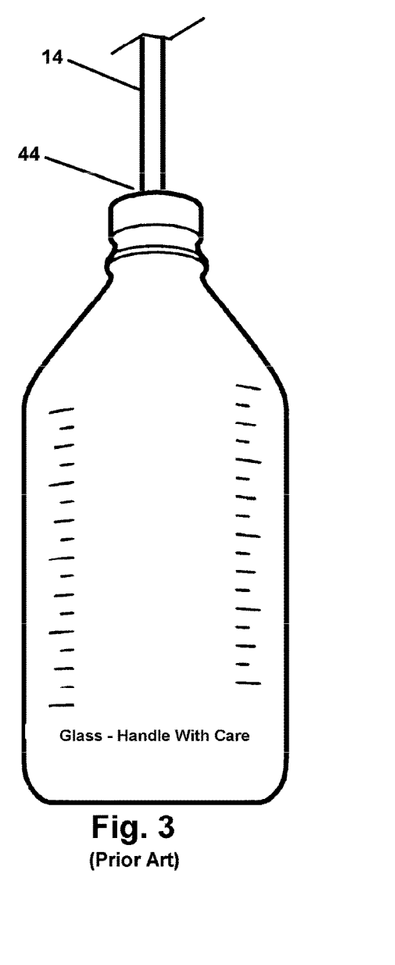
FIG. 3 shows the prior art glass container which uses a piercing connection end at the single container opening.

FIG. 3 shows the prior art glass container 42 which uses a piercing connection 44 end at the single container opening which as noted above has serious shortcomings in use.

Figures 4, 4A, 4B, 5:
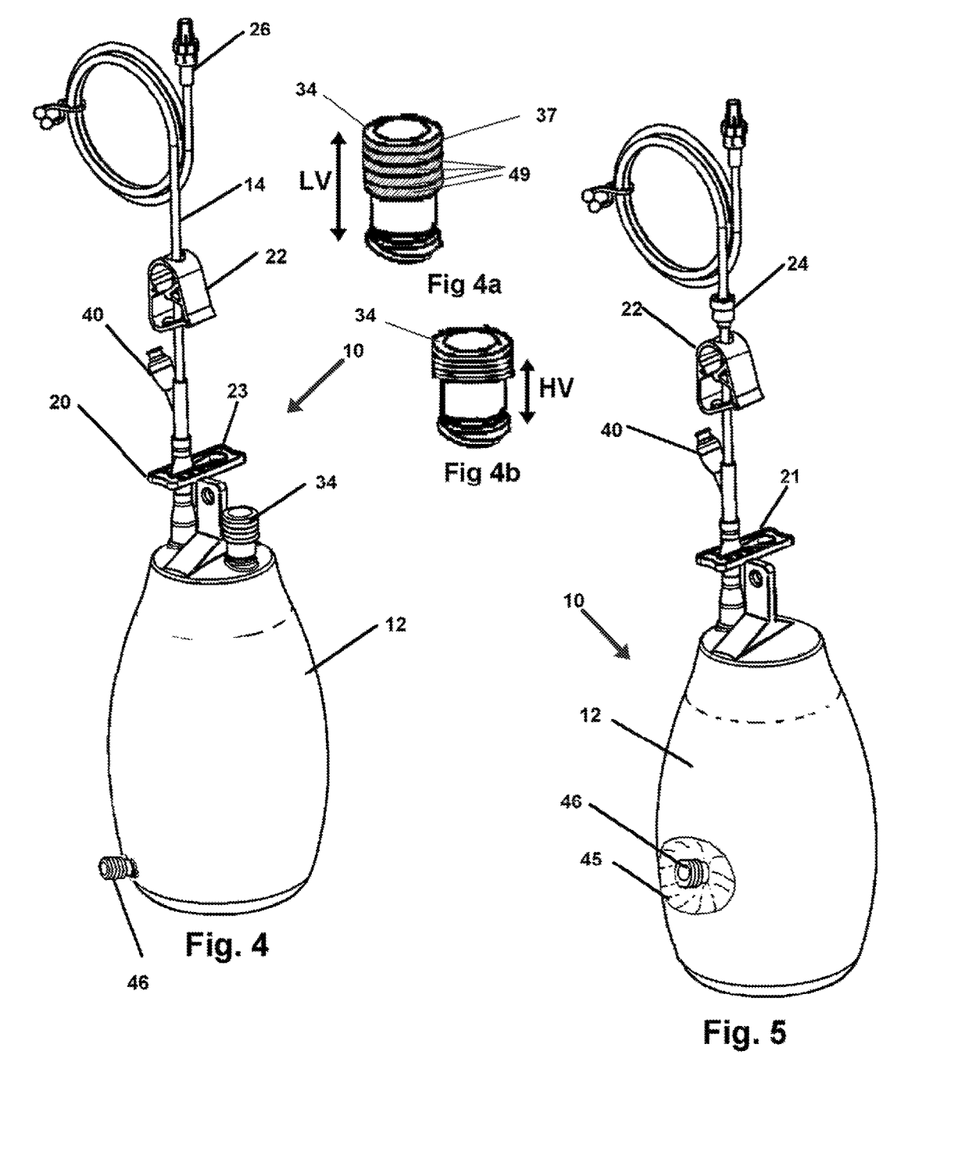
FIG. 4 shows the container similar to that of FIG. 1, but also having a projecting connector for engagement of secondary tubing or a syringe for sampling.
FIG. 4a depicts the vacuum gauge at a point of low interior vacuum of the container showing an extended configuration which may have colorized up-facing surfaces.
FIG. 4b depicts the gauge of FIG. 4a, when the interior container vacuum is high in a collapsed configuration and hiding the colorized surfaces.
FIG. 5 shows a container with a recessed connector for sealed removable engagement of secondary tubing or a syringe for sampling fluids.

FIG. 4 shows the container 12 similar to that of FIG. 1, but also having a projecting connector 46 for engagement of secondary tubing 14 for removal of fluid to a secondary container 14 or for sealed engagement with a syringe for sampling of fluid from a low point in the container 12.

FIG. 4a depicts the vacuum gauge 34 with the accordion style walls extended due to a point of low interior vacuum of the container. Upper facing surfaces 37 of the gauge 34, may be colorized, such as in red, to allow the user standing overhead to view the status of the container 12 more easily from such a distance and position. FIG. 4b depicts the vacuum gauge 48 of FIG. 4a, when the interior container 12 has vacuum level which is high and collapses the accordion sidewall.

FIG. 5 shows a container 12 with a recessed 45 projecting connector 46 similar to that of FIG. 4, for engagement with a leur fitting or other sealed engagement component such a syringe for fluid sampling, or a secondary tube 14 leading to a secondary container 12 for evacuating collected fluids as shown in FIG. 6 with another style container 12. The recessed projecting connector 46 is preferred because it prevents bumps and drops from breaking off the connector 46 during use or transport which as noted could spread contaminated fluid. A bayonet style, screw style, leur, or other connector capable of sealed engagement and allowing fluid and gas flow therethrough may be employed.

A backflow prevention valve 24 similar to that noted for the tube 14 may be engaged between the outlet of the connector 46 and the interior of the container 12 in any configuration herein, to prevent flow through the connector 46 unless the vacuum communicated to the distal end of the connector 46 is higher than the vacuum on the interior of the container 12. This prevents accidental leaks of fluid, and will prevent the vacuum within the container 12 to which the connector 46 is attached, from pulling air through the connector 46. The valve 24 would be configured to resist the maximum vacuum in the container 12 but open in the direction of a higher vacuum.

FIG. 6 shows another mode of the system herein employable with all containers 12, wherein a first container 12 is configured for patient engagement, and a second container 15 having a vacuum of sufficient strength to evacuate fluid from the first container 12, as well as reinstate the 600 to 900 hg/mm vacuum in the first container 12 may be engaged by sealed engagement of a communicating tube 14 between the containers. The connector 46 with the backflow prevention valve noted earlier would work especially well in this configuration where the vacuum in the second container 15 is higher than that of the first container 12 and will allow fluid flow into the second container 15 but not back into the first container 12.

An engageable clip 22 may preferably be provided for sealing the tube 14 until in sealed engagement between both containers, or stopping fluid flow from the first container 12 to the second container 15. The connectors 46 on both containers are configured for sealed engagement with cooperatively configured engageable connectors 47 on the tube 14. Also shown is an optional sampling position 51 formed on the sidewall of the first container 12 which may be pierced by a needle for sampling, but self seals thereafter.

The mode of the device 10 in FIG. 6, allows for the first container 12 engaged with a patient, to be drained and reinstated with a vacuum, without the need to disconnect it from the patient which is especially preferred.

The disclosed device has other applications, potentially, and one skilled in the art could discover these. The explication of the features of this invention does not limit the claims of this application; other applications developed by those skilled in the art will be included in this invention.

It is additionally noted and anticipated that although the device is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

While all of the fundamental characteristics and features of the fluid drainage system have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A fluid drainage system adapted for sealed engagement to a first end of a drainage tube which has an opposite end thereof positioned at a fluid drainage site in a patient, comprising:
    a first container, said first container having an interior defined by a sidewall in sealed engagement with an upper end of said first container and with a lower end of said first container;
    said interior cavity having a volume defined as an area between an interior surface of said upper end and an interior surface of said lower end which is surrounded by an interior surface of said sidewall;
    said first container having a useable configuration wherein negative air pressure is present within said interior cavity;
    a first connector extending from said upper end and having an axial conduit therethrough communicating between said interior cavity and an axial passage of an engaged tube configured at a first end thereof for sealed engagement to said first connector;
    a second end of said tube, configured for a sealed engagement of said axial passage, with said first end of said drainage tube;
    a secondary container having said negative pressure held within an internal cavity thereof;
    said secondary container positionable in a location remote from that of said first container, said secondary container having a connection, said connection having a pathway communicating with said internal cavity of said secondary container;
    said first container having a second connector positioned on said sidewall adjacent said lower end of said first container, said second connector having a second passageway communicating therethrough and through said sidewall to a communication with said internal cavity of said first container adjacent said lower end thereof;
    a conduit removably engageable with said connection on said secondary container and said second connector on said first container, between a disengaged position and an engaged position;
    said conduit, only while in said engaged position, placing said pathway of said connection in a sealed communication with said second passageway of said second connector;
    said conduit, while in said engaged position, communicating fluid adjacent said second passageway within said internal cavity of said first container, to said secondary container, whereby fluid within said internal cavity of said first container is removed to said secondary container; and
    whereby said negative pressure in said first container is renewed for continued use with said drainage tube of said patient without need for disconnection of said first end thereof from said first connector.

2. The fluid drainage system of claim 1, additionally comprising:
    said sidewall being formed in a curve;
    an upper portion of said sidewall extending in said curve between a perimeter edge of said upper end to a central area of said sidewall;
    a lower portion of said sidewall extending in said curve from said perimeter edge of said lower end to said central area of said sidewall;
    a circumference of said central area being larger than both said perimeter edge of said upper end and said perimeter edge of said lower end;
    an annular curved portion of said sidewall extending around said circumference of said central area of said;
    said annular curved portion of said sidewall formed by an outward curved area of said sidewall and an outward curved annular surface portion of said interior surface of said sidewall in a direction extending away from said interior cavity;
    said volume of said internal cavity being increased by an area of said outward curved annular surface portion of said interior surface of said sidewall surrounding said internal cavity; and
    said annular curved portion of said sidewall defining a structural reinforcement of said sidewall increasing a resistance to inward deflection of said sidewall from a force from said negative pressure in said internal cavity.

3. The fluid drainage system of claim 1, additionally comprising: a viewable gauge extending away from a first end thereof engaged with said upper end, said viewable gauge showing a measurement of remaining said negative pressure in said interior cavity;
    said viewable gauge having a central core communicating with said interior cavity through said upper end, said central core surrounded by an accordion style sidewall and an end;
    said accordion style sidewall having a plurality of circumferential folding portions each having downward surfaces which face away from said upper end of said first container which are opposite upward surfaces which face toward said upper end of said first container; and
    said viewable gauge having an elongated configuration caused by a lack of communication of negative pressure from said interior cavity to said central core;
    said upward facing surfaces being colorized in a color differing from that of a remainder of said sidewall;

said colorized upward facing surfaces of said sidewall only being viewable when said viewable gauge moves to said elongated configuration; and a presence of negative pressure in said interior cavity of said first container being discernable by a viewing said viewable gage prior to an operative engagement or disengagement from said drainage tube engaged with said patient.

4. A fluid drainage system adapted for sealed engagement to a first end of a drainage tube which has an opposite end thereof positioned at a fluid drainage site in a patient, comprising:

a first container, said first container having an interior cavity defined by a sidewall in sealed engagement with an upper end and a lower end;

said interior cavity having a volume defined as an area between an interior surface of said upper end and an interior surface of said lower end which is surrounded by an interior surface of said sidewall;

an annular curved portion of said sidewall extending around a circumference of said first container, in a central area of said sidewall located between said upper end and a lower end;

said annular curved portion of said sidewall being an outward curved portion of both said sidewall and said interior surface of said sidewall within said annular curved portion of said sidewall, in a direction extending away from said interior cavity and defining a widest area of said interior cavity;

said first container having a useable configuration wherein negative air pressure is present within said interior cavity;

said first container having a second connector positioned on a lower portion of said sidewall adjacent to said lower end of said first container, said second connector having a second passageway therethrough in communication with a lower end of said internal cavity of said first container located adjacent to and in contact with said interior surface of said lower end of said first container and surrounded by said lower portion of said sidewall;

said annular curved portion of said sidewall defining a structural reinforcement of said sidewall increasing a resistance to inward deflection of said sidewall from a force from said negative pressure in said internal cavity;

a first connector extending from said upper end and having an axial conduit therethrough communicating between said interior cavity and an axial passage of an engaged tube configured at a first end for sealed engagement to said first connector;

a second end of said tube, configured for a sealed engagement of said axial passage, with said first end of said drainage tube;

a sealing component having a first position blocking communication of a suction caused by said negative pressure in said interior cavity, through said axial passage to said second end of said tube, and having a second position, allowing communication of said suction to said axial passage;

a secondary container having said negative pressure held within an internal cavity thereof;

said secondary container having a connection, said connection having pathway communicating with said internal cavity of said second container;

a conduit removably engageable with said connection on said second container and said second connector on said first container, between a disengaged position and an engaged position;

said conduit, only while in said engaged position, placing said pathway of said connection in a sealed communication with said second passageway of said second connector;

said conduit, while in said engaged position, communicating fluid within said lower end said internal cavity of said first container, into said secondary container, whereby fluid when within said lower end of said internal cavity of said first container, is removable to said internal cavity of said secondary container whereby said negative pressure in said first container is renewed; and whereby said fluid drainage system is engageable to said drainage tube with said sealing component in said first position, without loss of negative pressure in said interior cavity, and can communicate said suction to draw fluid from said patient to said interior cavity with said sealing component in said second position.

5. The fluid drainage system of claim 4, additionally comprising:

said sidewall of said first container formed in an outward arch extending away from said interior cavity and communicating between said upper end and said lower end; and said annular curved portion of said interior surface of said sidewall within said annular curved portion of said sidewall forming said widest portion of said interior cavity which is centered between two respective narrower portions of said interior cavity, a first said narrower portion located between said upper end and said outward arch and a second said narrower portion located between said lower end and said outward arch.

6. The fluid drainage system of claim 4, additionally comprising:

a viewable gauge extending away from a first end thereof engaged with said upper end, said viewable gauge showing a measurement of remaining said negative pressure in said interior cavity;

said viewable gauge having a central core communicating with said interior cavity through said upper end, said central core surrounded by an accordion style sidewall and an end;

said accordion style sidewall having a plurality of circumferential folding portions each having downward surfaces which face away from said upper end of said first container which are opposite upward surfaces which face toward said upper end of said first container; and said viewable gauge having an elongated configuration caused by a lack of communication of negative pressure from said interior cavity to said central core;

said upward facing surfaces being colorized in a color differing from that of a remainder of said sidewall;

said colorized upward facing surfaces of said sidewall only being viewable when said viewable gauge moves to said elongated configuration; and a presence of negative pressure in said interior cavity of said first container being discernable by a viewing said viewable gage prior to an operative engagement or disengagement from said drainage tube engaged with said patient.

* * * * *